US00PP14764P2

(12) United States Plant Patent
Sherman

(10) Patent No.: US PP14,764 P2
(45) Date of Patent: May 4, 2004

(54) PEACH TREE NAMED 'UFSUN'

(50) Latin Name: *Prunus persica*
Varietal Denomination: UFSun

(75) Inventor: Wayne B. Sherman, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 12 days.

(21) Appl. No.: 10/619,292

(22) Filed: Jul. 15, 2003

(51) Int. Cl.[7] ..... A01H 5/00
(52) U.S. Cl. ..... Plt./197
(58) Field of Search ..... Plt./197

*Primary Examiner*—Anne Marie Grunberg
*Assistant Examiner*—June Hwu

(57) ABSTRACT

'UFSun' is a new and distinct variety of peach tree which has a winter chilling requirement of approximately 100 to 150 chill units (cu). The tree is large size, highly vigorous with a semi-spreading growth habit, and bears showy pink flowers. Glands are small and reniform in shape and isolated to the basal portions of leaves. Trees of 'UFSun' bear heavy annual crops of early season fruit which are medium size for its ripening season. Fruit have firm, yellow, non-melting flesh which is clingstone. Fruit are uniform, attractive, substantially symmetrical shape, and have an attractive 50 to 60% red skin with darker red stripes. The fruit ripens about 80 to 85 days from bloom, with 'Flordaprince', and in late April at Immokalee and Gainesville, Fla.

1 Drawing Sheet

BOTANICAL CLASSIFICATION *Prunus persica*—'UFSun'.

BACKGROUND OF THE NEW VARIETY

The present invention relates to a new and distinct variety of peach (*Prunus persica* (L.) Batsch) tree which is named 'UFSun' and, more particularly to a peach tree which produces good eating quality, clingstone, non-melting and yellow flesh fruit which are mature for fresh market in mid-April at Immokalee, and in late April in Gainesville, Fla., and which are produced on a tree adapted to a mild winter climate. Contrast is made to 'Flordaprince' (unpatented) peach tree, a standard variety, for reliable description. This new variety is a promising candidate for commercial success in that it retains fruit firmness at the full flavor, tree ripe stage for 10 days on the tree.

ORIGIN OF THE VARIETY

This peach tree (genotype) originated in a cultivated area of the fruit breeding program at the University of Florida, located at Gainesville, Fla. The seed parent was 'Fla. 90-50CN' (unpatented), a non-melting flesh nectarine [originated as an F2 of (Fla 84-18C ×Fla. 9-20C)] (both unpatented peaches of complex origin). The pollen parent was 'UFGold' (U.S. Plant Pat. No. 10,315). 'UFSun' peach tree was selected in 1998, designated as Fla. 97-20C, propagated asexually in Gainsville, Fla. by budding on 'Flordaguard' (unpatented) seedling rootstock, and tested at Gainesville and Immokalee, Fla. Asexually propagated plants remain true to the original tree and all characteristics of the tree and the fruit were transmitted. Trees of 'UFSun' bloom early at Gainesville and the crop is often lost to spring frost, but it was determined at Immokalee to have plant adaptation with unique fruit characteristics making it worthy for commercial fresh fruit production.

SUMMARY OF THE VARIETY

'UFSun' peach tree is a new and distinct variety that bears yellow, non-melting flesh fruit, and has a low chilling endodormancy requirement. It blooms with 'Flordaprince' peach tree at Immokalee, bearing an attractive red over a deep yellow ground color. The estimated chilling requirement is 100 to 150 chill units, the same as 'Flordaprince'.

The present invention resulting in 'UFSun' peach tree is characterized by fruit of excellent flavor and eating quality. The trees are vigorous, productive and without alternate bearing. Trees attain in two years, a height of three meters and a spread of two meters at Immokalee. Terminal growth of up to a meter annually is common on mature 4-year-old trees with normal pruning to a vase shape. The first fruit ripen in mid-April at Immokalee and in late April at Gainesville or about 80 days from full bloom, which is about the same time as 'Flordaprince'. The fruit are uniformly medium-large size for an early season peach. Ripe fruit have about 50% (with darker stripes) red skin. There is no red pigment in the flesh at the pit. The flower anthers are orange, a common characteristic of other standard peach and nectarine varieties.

DESCRIPTION OF THE DRAWINGS

The accompanying drawing is a color photograph which shows a typical specimen of the fruit, leaf, and stem of the new variety as nearly true as it is reasonably possible to make in a color illustration of this type. The photograph shows an attractive shape and exterior coloration of six specimens of fruit above a ruler in a stem end view, a blossom end view, side views facing and perpendicular to the suture, and 2 fruit cut longitudinally showing the flesh with a clingstone pit in place.

DETAILED BOTANICAL DESCRIPTION

The tree, flowers, and fruit may vary in slight detail due to variations in soil type, cultural practices, and climatic condition. The potential for commercial production of fresh fruit by 'UFSun' peach tree is high, due to its attractive red skin over a deep yellow ground color, large fruit of good flavor balance between sugar and acid, and exceptional firmness due to its non-melting flesh. The present botanical description is that of the variety as grown on 4-year-old trees grown on 'Flordaguard' rootstock under the ecological conditions prevailing at Gainesville, Fla. Variations of the usual magnitude and characteristics incident to changes in climatic growing conditions, soils, fertilization, pruning, irrigation, and pest control are to be expected. Colors (except those in common terms) are described from "The Pantone Book of Color" published by H. N. Abrams, Inc., N.Y. 1990.

Tree:

*Ploidy.*—Diploid.

*Size.*—Trees are large when trained to an open vase form.

*Vigor.*—Vigorous, and must be summer and winter pruned to keep tree height restricted and to keep center of vase open. Trees respond typically to irrigation and fertilization. Tree growth of 5 to 7 feet in height and 4 to 6 feet in width occurs in the first growing season in the field. Annual growth on mature trees averages 2 to 4 feet in length.

*Density.*—Medium to dense in branching habit and requires pruning to open the tree center which permits high sunlight entrance for enhancing fruit color and sugar.

*Form.*—Spreading, in contrast to upright for 'Flordaprince'.

*Hardiness.*—Hardy with respect to typical north central Florida winters. Chill units during endodormancy is estimated at 100 to 150 cu.

*Productivity.*—Annual and regular without alternate bearing and must be fruit thinned to avoid limb breakage and obtain largest fruit size. Trees annually set several times the number of fruit for a desired crop load.

Trunk:

*Size.*—Large trunk diameter attaining 14–16 cm diameter at a height of 30 cm above ground at the end of 4 years growth.

*Bark texture.*—Medium smooth, but changes to medium rough as tree ages.

*Bark color.*—Variable with older bark considered mostly gray, Chinchilla (Pantone 17-1109).

*Lenticels.*—Numerous 28 per 4 square inches of surface area of trunk, large (4 to 8 mm length), perpendicular to the trunk with the center being Puddy (Pantone 13-0711).

Branches:

*Size.*—Strong growth of scaffold branches. This is not distinctive of the variety.

*Texture.*—Relatively smooth, medium amount of lenticels attaining size found on trunk and old scaffolds. Roughness increases with age.

*Color.*—New wood is light green, Tarragon (Pantone 15-0326) on the underside with anthocyanin on the sunny upper surface, Pink Sand, (Pantone 15-1318); Two-year-old wood is more brown, Cedar Wood (Pantone 17-1525).

*Crotch angles.*—Angles selected at 45 to 70 degrees in first year of tree training. Natural angles are within the normal range of standard varieties for a semi-spreading tree.

Leaves:

*Size.*—Medium; 18 to 20 cm length, including petiole; 3.5 to 3.8 cm width. Measurements were made on full size leaves of vigorous upright shoots in summer growth.

*Thickness.*—Regular and average for many peach varieties. Not distinctive of the variety.

*Form.*—Lanceolate.

*Apex.*—Acuminate.

*Margin.* —Serrulate, slightly undulate.

*Base.*—Cuneate.

*Surface.*—Upper, glabrous; Lower, medium large veins that are pinnately netted.

*Color.*—Lower surface is green, Peridot (Pantone 17-0336); Upper surface is slightly darker green, Black Forest (Pantone 19-0315).

*Glands.*—Two to four reniform glands mostly on lower leaf blade, but occasionally on petiole. Leaf glands are average size for many peach varieties, not distinctive for the variety, and on young full size leaves are Lettuce Green (Pantone 13-0324) in mid summer.

*Petiole.*—Ranges 10 to 11 mm) length; 2 mm diameter. Lettuce Green (Pantone 13-0324) in mid summer. Two longitudinal grooves on the ventral side.

*Stipules.*—Medium in length (8 to 10 mm), 2 per node, and abscising (deciduous) just before leaf obtains full size on summer growth, both common to most peach varieties.

*Arrangement.*—Alternate.

Flower buds:

*Hardiness.*—Hardy with respect to north central Florida winters. No damage observed in winter following a minimum of 16F.

*Abundance.*—Moderately high, most buds set fruit in absence of spring frosts.

*Size.*—Medium, average 3.5 mm length in late autumn.

*Form.*—Plump, conic, and free in late summer, elongating by winter. Shape is obtuse.

*Surface.*—Pubescent scales.

*Color.*—Brown, Bitter Chocolate (Pantone 19-1317) in late autumn.

Flowers:

*Blossom period.*—With 'Flordaprince' peach — average January 20–25 at Immokalee, occurring over a 7 to 10 day period, dependant on ambient temperatures.

*Aroma.*—Fragrance is slight to none.

*Type.*—Showy, location and seasonally variable size, but within the range of commercial varieties. Average flower diameter 32 mm. Average petal length 16 mm; width, 11 mm. Petals are obovate and edges vary from smooth to slightly undulate.

*Color.*—Petals are Peach Melba (Pantone 14-1418) upon opening, fading at the outer edges before abscising, and within the range of standard varieties.

*Flower parts.*—Pistil shape and color are within the range of standard commercial varieties. Pistils are usually 1 per flower and pubescent. Pistils length (from tip of stigma to base of the ovary) is 13 mm and color is pale green, Pale Star (Pantone 12-0626). There are 5 sepals and 5 petals. Sepals are pubescent and petals glabrous. Flower pedicel is 2 to 3 mm length, not distinguishing for the variety.

*Stamens.*—Number varies from 27 to 40. Length is 8 to 11 mm.

*Anthers.*—Orange, Persimmon Orange (Pantone 16-1356) at flower opening, regular size.

*Pollen.*—Abundant and yellow, Cornsilk (Pantone 13-0932).

*Calyx cup.*—Medium (5 mm diameter and 6 mm depth) as compared to commercial varieties.

*Fertility.*—Self fertile and no cross pollination is required.

Fruit:

*Maturity when described.*—Tree ripe, April 25, 2003 at Gainesville.

*Date of first picking.*—April 22, 2003 at Gainesville.

*Date of last picking.*—May 3, 2003 at Gainesville.

*Size.*—Uniform, medium (medium-large size for early season maturity at 110 to 130 g). Varies with number of fruit per tree, soil type, climatic conditions and cultural practices. Average equatorial diameter. — 2⅜ inches (61 mm). Average polar length (stem to distal end). — 2¼ inches (56 mm).

*Pedicel.*—Length is 7 to 9 mm; Width is 3 to 4 mm. Color is light green, Dried Moss (Pantone 14-0626). Pedicel is enlarged at point of fruit attachment.

*Longitudinal section form.*—Round to slightly squat.

*Transverse section through diameter.*—Round.

*Suture.*—Inconspicuous in form and color.

*Ventral surface.*—Usually rounded.

*Base.*—Slightly retuse.

*Apex.*—Usually rounded to slight obtuse.

*Crater at pedicel attachment.*—Flaring circular, but elongated in the suture plane. Stem depressing on base of fruit. Depth is 10 mm; Breadth is 22 mm at top and 3 to 4 mm at pedicel attachment.

Skin:

*Thickness.*—Medium in comparison to commercial peach varieties.

*Texture.*—Medium in comparison to commercial peach varieties.

*Tenacity.*—Tenacious to flesh.

*Color.*—Bright red, Mandarine Red (Pantone 17-1562) with darker red stripes, Ginger (Pantone 17-1444) over 50 to 60% of skin surface at harvest. Ground color deep yellow, Radiant Yellow (Pantone 15-1058). Fruit exposed to sunlight have a higher degree of enhanced red skin.

*Tendency to crack.*—None observed.

*Taste.*—No astringency observed.

*Pubescence.*—Short and medium soft.

Flesh:

*Ripens.*—Evenly within each fruit.

*Texture.*—Firm, fine, juicy, and non-melting when fully ripe.

*Fibers.*—Very fine, small, tender and abundant throughout the flesh.

*Aroma.*—Moderate and in the middle range of commercial peach varieties.

*Eating quality.*—Good, sweet, slightly acid. Fruit averaged 11 brix when described. Titratable acidity was 0.60 as % malic acid and penetrometer firmness was 1.4 kg as measured with a standard 8 mm tip at harvest. No over-ripe off-flavors noted.

*Juice.*—Abundant.

*Color.*—Deep yellow, Sunset Gold (Pantone 13-0940). Fruit exposed to full sunlight often have anthocyanin in the fruit of the outer half of the flesh orange-red, Flamingo (Pantone 16-1450) There is no red at the pit.

*Browning by oxidation.*—Slight on tree ripe fruit beginning to soften.

*Amygdalin.*—Undetected.

Stone:

*Type.*—Clingstone, adhering to flesh even at softening.

*Size.*—Medium small; average length is 30 mm, average width at the equator perpendicular (dorsal to ventral side) to the suture is 22 mm, average width at the equator across (facing) the suture is 17 mm. Average pit wall thickness at the equator perpendicular to the suture is 4 to 5 mm.

*Color.*—Light brown, Buckskin (Pantone 16-1342) when freshly exposed.

*Form.*—Elliptic shape with an acute base and acuminate apex.

*Sides.*—Near equal.

*Surface.*—Irregularly furrowed toward the ventral edge from apex to base. Pitted from the center toward the base and apex.

*Ridges.*—Almost nonexistent, even on the suture side.

*Tendency to split.*—None observed.

*Kernel.*—Oval shape, bitter (amygdalin is abundant) and viable, but low germination without embryo culture. Average width, 8 mm; Average length 14 mm. Color Cream, Ivory (Pantone 11-0907) on mature fruit when first removed from stone of freshly harvest fruit.

Use: Fresh; dessert. Market — local and long distance.

Shipping and keeping quality: Good, fruit hold firm in cold storage for 2 weeks at 38 to 42 F without internal breakdown of flesh or appreciable loss of eating quality. Picking and packing gave minimum bruising and scarring of fruit.

Resistance to disease: High resistance to bacterial spot incited by *Xanthomonas campestris* pv. *pruni* (E. F. Smith) Dye. Susceptible to leaf rust incited by Tranzschelia discolor (Fuckel) Tranzschel & Litvinov. Resistance to other fruit and tree diseases are within the range for commercial cultivars. No unusual resistance or susceptibility to insects and diseases noted.

We claim:

1. A new and distinct peach tree as illustrated and described, characterized by a low chilling requirement, and bearing early mid-season fruit having firm, yellow and non-melting flesh of high eating quality, and an attractive, 50% red over deep yellow ground color on skin of fruit ripening in late April with 'Flordaprince' at Immokalee and Gainesville, Fla.

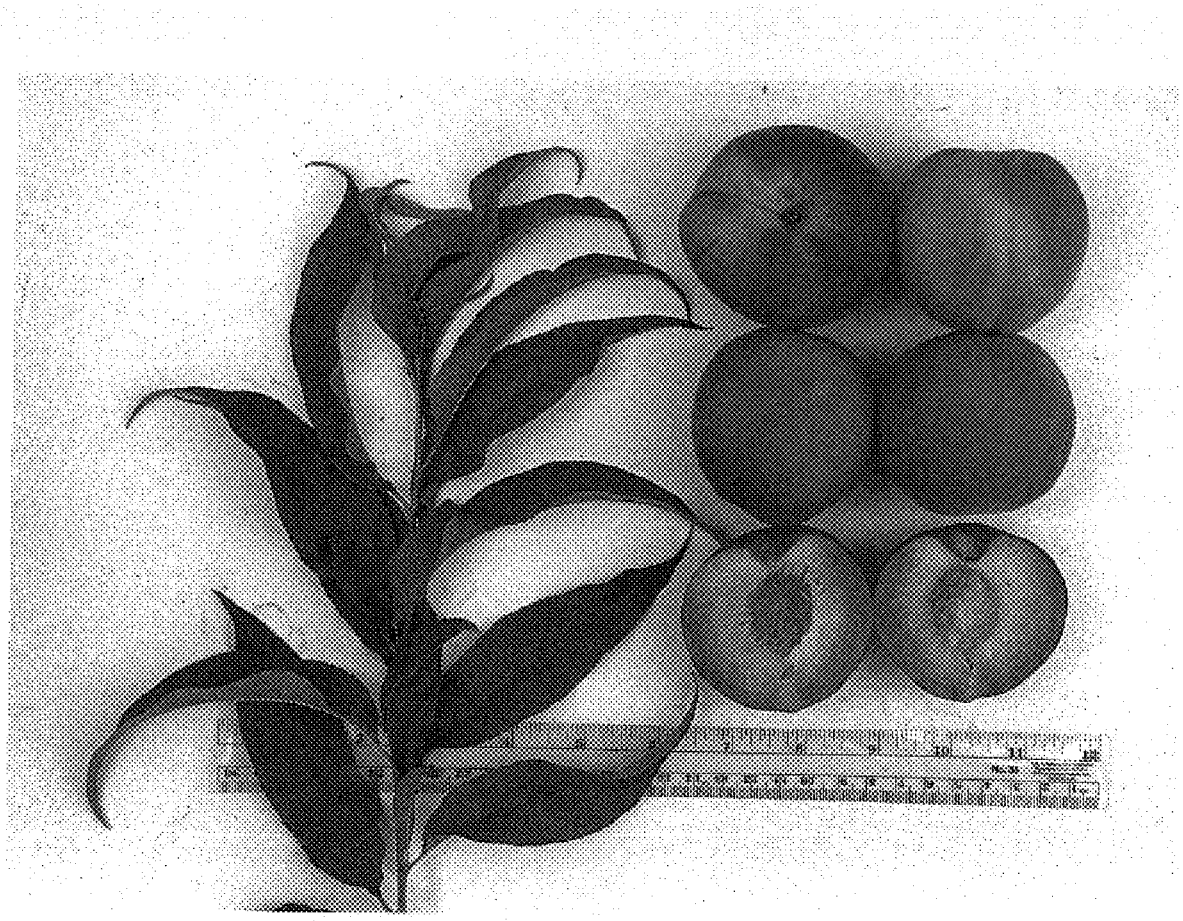

* * * * *